US007764170B2

(12) United States Patent
Yi (10) Patent No.: US 7,764,170 B2
(45) Date of Patent: Jul. 27, 2010

(54) SYSTEM AND METHOD FOR EMERGENCY ALARM (75) Inventor: Kyoung-soo Yi, Goyang-si (KR)

(73) Assignee: Seyfarth Shaw LLP, Chicago, IL (US)

( * ) Notice: Subject to any disclaimer, the term of this patent is extended or adjusted under 35 U.S.C. 154(b) by 363 days.

(21) Appl. No.: 11/760,890

(22) Filed: Jun. 11, 2007

(65) Prior Publication Data
US 2007/0285226 A1 Dec. 13, 2007

(30) Foreign Application Priority Data
Jun. 12, 2006 (KR) ...................... 10-2006-0052429

(51) Int. Cl.
G08B 1/08 (2006.01)
(52) U.S. Cl. .............................. 340/539.11; 340/539.1; 340/539.12
(58) Field of Classification Search ............ 340/539.12
See application file for complete search history.

(56) References Cited

U.S. PATENT DOCUMENTS

| | | | | |
|---|---|---|---|---|
| 3,795,896 | A * | 3/1974 | Isaacs | 340/825.36 |
| 5,873,369 | A * | 2/1999 | Laniado et al. | 600/300 |
| 5,917,414 | A * | 6/1999 | Oppelt et al. | 340/573.1 |
| 5,940,004 | A * | 8/1999 | Fulton | 340/825.49 |
| 6,198,394 | B1 * | 3/2001 | Jacobsen et al. | 340/573.1 |
| 6,301,484 | B1 | 10/2001 | Rogers et al. | |
| 6,840,904 | B2 * | 1/2005 | Goldberg | 600/300 |
| 2003/0176798 | A1 | 9/2003 | Simon | |
| 2004/0017300 | A1 | 1/2004 | Kotzin et al. | |
| 2004/0109558 | A1 * | 6/2004 | Koch | 379/373.01 |
| 2005/0075542 | A1 | 4/2005 | Goldreich | |
| 2005/0096094 | A1 * | 5/2005 | Kim et al. | 455/566 |
| 2005/0203349 | A1 * | 9/2005 | Nanikashvili | 600/300 |
| 2005/0288563 | A1 * | 12/2005 | Feliss et al. | 600/300 |
| 2006/0255922 | A1 * | 11/2006 | Taki et al. | 340/438 |

FOREIGN PATENT DOCUMENTS

| | | |
|---|---|---|
| EP | 1 519 619 | 3/2005 |
| JP | 08089483 | 4/1996 |
| JP | 11-112695 A | 4/1999 |

(Continued)

OTHER PUBLICATIONS

Marek Malik, et al., "Heart Rate Variability", Standards of measurement, physiological interpretation, and clinical use, European Heart Journal, vol. 17, Mar. 1996, pp. 354-381.

(Continued)

Primary Examiner—Benjamin C Lee
Assistant Examiner—Curtis J King
(74) Attorney, Agent, or Firm—Cantor Colburn LLP (57) ABSTRACT

An emergency alarm system is provided, including: a mobile communication terminal to measure and transmit a user's bio signal and to output sound data with a bell sound when an emergency alarm signal is received from a health care server; and a health care server to determine from the bio signal whether or not the user is in an emergency, and to transmit an emergency alarm signal to the mobile communication terminal when the user is determined to be in an emergency.

10 Claims, 3 Drawing Sheets

FOREIGN PATENT DOCUMENTS

| | | |
|---|---|---|
| JP | 2000124989 | 4/2000 |
| JP | 2001-344352 A | 12/2001 |
| JP | 2002-009683 A | 1/2002 |
| JP | 2002078005 | 3/2002 |
| JP | 2003224674 | 8/2003 |
| JP | 2003296248 | 10/2003 |
| KR | 1020010044501 | 6/2001 |
| KR | 10-2001-0093986 | 10/2001 |
| KR | 1020040098982 | 11/2004 |
| KR | 1020060033223 | 4/2006 |
| KR | 1020060037537 | 5/2006 |
| KR | 1020060037538 | 5/2006 |

OTHER PUBLICATIONS

English Translation of Office Action issued Jul. 31, 2009 for corresponding Chinese Patent Application No. 200710110995.7. Note that the three (3) U.S. Patents cited therein [US 3,795,896 to Isaacs; US 5,940,004 to Fulton; and US 6,840,904 to Goldberg] were cited by the Examiner in the Office Action dated Jun. 26, 2009 for the instant application.

* cited by examiner

SYSTEM AND METHOD FOR EMERGENCY ALARM

CROSS REFERENCE TO RELATED APPLICATION

This application claims the benefit of and priority from Korean Patent Application No. 2006-052429, filed on Jun. 12, 2006, which is hereby incorporated by reference for all purposes as if fully set forth herein.

BACKGROUND OF THE INVENTION

1. Field of the Invention

The present invention relates to a mobile communication terminal and, more particularly, to a mobile communication terminal having an emergency alarm function to notify of a user's emergency.

2. Discussion of the Background

Patients suffering from hypertension, heart disease, diabetes etc. need to take a medical checkup at regular intervals to provide for contingencies, such as unexpected death.

Korean Laid-Open Patent Application No. 2001-093986 discloses a health care method in which a user transmits his or her bio signal at a remote place without visiting a hospital and a health care server manages the bio signal.

The above-mentioned method relates to an integrated medical data management system over a network, in which medical terminals at medical centers and subscriber terminals are connected to each other through networks through which medical information is integrated, managed and served in real time.

However, the above-mentioned method does not disclose how to deal with patients or users who become unconscious at unfrequented places and have to receive immediate attention.

European Heart Journal (1996) publishes a paper titled "Heart Rate Variability—Standards of Measurement, Physiological Interpretation, and Clinical Use", in which various physiological phenomena can be monitored through analyzed ECG waveforms through which it is possible to enhance risk stratification of sudden cardiac death. This paper discloses standard parameters and measurement units for ECG waveform analysis, and the implication of bio indices studied until now.

According to the paper, bio indices can be monitored by analyzing heart rate variability (HRV) of ECG waveforms on time and frequency domains. Among the indices related to the time domain analysis, the standard deviation of NN interval (SDNN) indicates the standard deviation of ECG waveform over 24 hours, which reflects the innate capacity of heart reacting to hormone.

SUMMARY OF THE INVENTION

The present invention provides a method for notifying of an emergency when a user needs immediate attention.

Additional features of the invention will be set forth in the description which follows, and in part will be apparent from the description, or may be learned by practice of the invention.

The present invention discloses an emergency alarm system including: a mobile communication terminal to measure and transmit a user's bio signal and to output sound data with a bell sound when an emergency alarm signal is received from a health care server; and a health care server to determine from the bio signal whether or not the user is in an emergency, and to transmit an emergency alarm signal to the mobile communication terminal when the user is determined to be in an emergency.

The present invention also discloses an emergency alarm system having a mobile communication terminal including: a bio-signal measurement unit to measure a user's bio signal; a data storage unit to store sound data notifying an emergency; an emergency determination unit to determine based on the bio signal measured by the bio-signal measurement unit whether or not the user is in an emergency condition; a control unit to output one of the sound data with bell sound stored in the data storage unit when the user is determined to be in an emergency condition; and a data output unit to regenerate the sound data outputted from the control unit into an audible sound and output the audible sound through a speaker.

The present invention also discloses an emergency alarm method in a mobile communication terminal, including: measuring a user's bio signal; transmitting the bio signal outside and receiving an emergency alarm signal from a health care server; and outputting sound data with bell sound stored in a data storage unit when the emergency alarm signal is received.

The present invention also discloses an emergency alarm method in a health care server, including: receiving a bio signal; determining based on the bio signal whether or not a user's health condition is in an emergency; and generating and transmitting an emergency alarm signal to a mobile communication terminal when the user is determined to be in an emergency condition.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

The invention is described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

It will be understood that when an element or layer is referred to as being "on" or "connected to" another element or layer, it can be directly on or directly connected to the other element or layer, or intervening elements or layers may be present. In contrast, when an element is referred to as being "directly on" or "directly connected to" another element or layer, there are no intervening elements or layers present.

Figure 1:
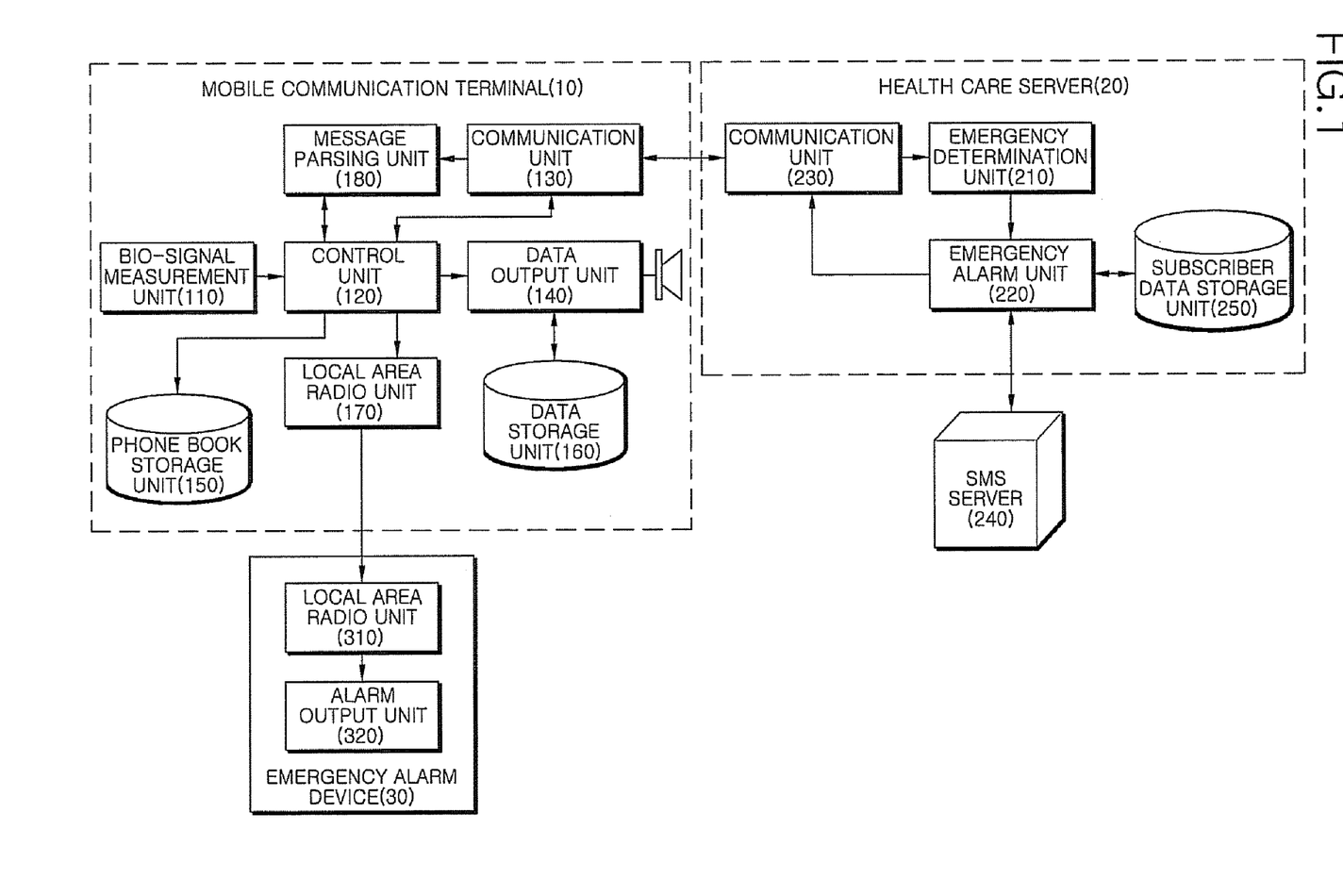
FIG. 1 is a block diagram of an emergency alarm system according to an exemplary embodiment of the invention.

FIG. 1 is a block diagram of an emergency alarm system according to an exemplary embodiment of the invention.

The emergency alarm system includes a mobile communication terminal 10 and a health care server 20. The mobile communication terminal 10 measures and transmits a bio signal of a user, and outputs sound data with bell sound when an emergency alarm signal is received from a health care server. The health care server 20 determines from the bio signal transmitted from the mobile communication terminal 10 whether or not the user is in an emergency condition, and transmits an emergency alarm signal to the mobile communication terminal 10 in case of emergency.

Examples of the mobile communication terminal 10 include personal digital assistant (PDA), cellular phone, personal communications service (PCS) phone, global system for mobile communication (GSM) phone, wideband code division multiple access (W-CDMA) phone, and CDMA-2000 phone.

A user uses his or her own mobile communication terminal 10 to monitor and measure his or her bio-index anytime, anywhere. Measurement data is transmitted to the health care server 20 by one key stroke on a monitor. Furthermore, the mobile communication terminal 10 may transmit bio-index data to the health care server 20 at regular intervals. When receiving an emergency signal from the health care server 20, the mobile communication terminal 10 regenerates and outputs sound data.

The health care server 20 is a computer installed in a medical center, and monitors the bio-index through an expert system. The user can check his or her bio-index graph through a website. Furthermore, an attending doctor can check his or her patient's bio-index graph and make a diagnosis at a remote place.

The health care server 20 monitors a user's bio signal received from the mobile communication terminal 10 at regular intervals, and transmits an emergency signal to the mobile communication terminal 10 in case of emergency. Accordingly, it helps prevent dangerous heart-related conditions such as heart attack or stroke.

The mobile communication terminal 10 includes a bio-signal measurement unit 110, a data storage unit 160, a communication unit 130, a control unit 120, and a data output unit 140. The bio-signal measurement unit 110 measures a user's bio-signal. The data storage unit 160 stores sound data which alarms an emergency. The communication unit 130 communicates with the health care server 20. The control unit 120 transmits a bio signal measured by the bio-signal measurement unit 110 through the communication unit 130, and outputs one of the sound data with bell sound stored in the data storage unit 160 when an emergency alarm signal is received from the health care server 20. The data output unit 140 regenerates the sound data from the control unit 120 into an audible sound and outputs the audible sound through a speaker.

The bio-signal measurement unit 110 may include an electrocardiogram (ECG) system. The ECG system may include an electrode unit, which includes a plurality of electrodes attached to a patient's body to detect an electric signal, an analog signal processor, which detects a bio potential from the electric signal, and a digital signal processor, which converts analog data from the analog signal processor into digital data. The bio-signal measurement unit 110 may further include other systems which measure bio signals to check the user's health condition, such as blood pressure level or blood glucose level.

The data storage unit 160 is a flash memory and stores sound data which is downloaded from a computer or a website. The data storage unit 160 stores at least one sound data to notify of the user's emergency. For example, the sound data may have voice data, such as "I am in an unconscious condition. Please help me" or "I am in hypoglycemia shock. Please give me candy or sugar".

The communication unit 130 includes an antenna and an RF circuit to communicate with a base transceiver station (BTS). When a signal is received over the antenna, the communication unit 130 downconverts the signal and outputs the downconverted signal to the control unit 120. The communication unit 130 upconverts data from the control unit 120 and transmits a radio signal to the BTS over the antenna.

The control unit 120 includes a digital signal processor (DSP), a microprocessor and other circuits, and generally controls the mobile communication terminal. Baseband circuits of the communication unit 130 and most circuits of the control unit 120 are provided as integrated circuits and are commercially available. The integrated circuits typically named as MSM chips include hardware dedicated for communications, digital signal processor, and common microprocessor. Components constituting the control unit 120 may be made in the form of hardware or software, or in combination of hardware and software.

The control unit 120 transmits a bio signal measured by the bio-signal measurement unit 110 to the health care server 20 through the communication unit 130. When receiving an emergency alarm signal from the health care server 20, the control unit 120 converts one of the sound data stored in the data storage unit 160 into a bell sound and outputs the bell sound.

When receiving the emergency alarm signal from the health care server 20, the control unit 120 outputs the sound data with a maximum level of volume. When outputting the sound data, the control unit 120 controls the data output unit 140 to regenerate the sound data with a maximum level of volume. For example, the data output unit 140 may include an amplifier to amplify the sound data to have its maximum volume.

The data output unit 140 regenerates one of the sound data stored in the data storage unit 160 into an audible sound. The data output unit 140 includes a decoder, which decodes the sound data outputted from the control unit 120, a D/A converter, which converts the decoded digital audio signal into an analog signal, and a speaker, which amplifies the analog signal into an audible sound and outputs the audible sound.

The mobile communication terminal 10 further includes a phone-book storage unit 150 which stores calling numbers and sound data corresponding to the calling numbers. The control unit 120 selects sound data with bell sound corresponding to a calling number of an emergency alarm signal based on data stored in the phone-book storage unit 150, and outputs the bell sound.

The phone-book storage unit 150 may be a flash memory which stores data, such as phone book and messages. The phone-book storage unit 150 stores a calling number of the health care server 20, and sound data to be regenerated when an emergency alarm signal is received from the calling number. For example, sound data "I am in an unconscious condition. Please help me" corresponds to calling number 000-1234, and "I am in hypoglycemia shock. Please give me candy or sugar" corresponds to another calling number 000-1233.

When receiving an emergency alarm signal, the control unit 120 detects its corresponding calling number, and selects sound data with bell sound which corresponds to the calling number based on information stored in the phone-book storage unit 150. That is, in addition to the bell sound to call for help, immediate medical treatment can be provided for the unconscious user.

The mobile communication terminal 10 further includes a local area radio unit 170. When the control unit 120 selects and outputs sound data with bell sound and no signal is input for a predetermined time, the mobile communication terminal 10 outputs an emergency alarm signal through the local area radio unit 170. An emergency alarm system further includes an emergency alarm device 30 including a local area radio unit 310, which receives an emergency alarm signal from the mobile communication terminal 10, and an alarm output unit 320, which outputs an emergency alarm when receiving the emergency alarm signal from the local area radio unit 310.

The local area radio unit 170 may be a Bluetooth module. The Bluetooth module is one which enables communication with a Bluetooth device. The local area radio unit 170 transmits an emergency alarm signal with 2.4 GHz Industrial Scientific Medical (ISM) bandwidth according to Bluetooth protocol over an antenna. The local area radio unit 170 may use IrDA or ZigBee.

The emergency alarm device 30 includes a local area radio unit 310, which receives an emergency alarm signal from the mobile communication terminal 10, and an alarm output unit 320, which outputs an emergency alarm when receiving the emergency alarm signal from the local area radio unit 310.

The local area radio unit 310 makes data communication with the local area radio unit 170 of the mobile communication terminal 10.

The alarm output unit is driven with battery power of the emergency alarm device 30, and produces a sound of about 140 dB. The alarm output unit 320 preferably produces a sound larger than the mobile communication terminal 10. The emergency alarm device 30 is made in form of a wrist watch, a necklace, or an accessory of the mobile communication terminal 10 so that it is convenient for the user to carry.

The health care server 20 includes a communication unit 230, an emergency determination unit 210, and an emergency alarm unit 220. The communication unit 230 receives a bio signal from the mobile communication terminal 10. The emergency determination unit 210 determines whether or not a user is in an emergency condition based on the bio signal from the communication unit 230. The emergency alarm unit 220 generates an emergency alarm signal when it is determined to be an emergency by the emergency determination unit 210, and transmits the emergency alarm signal to the mobile communication terminal 10 through the communication unit 230.

The communication unit 230 includes an antenna and an RF circuit to communicate with a base transceiver station, and makes data communication with the communication unit 130 of the mobile communication terminal 10.

The emergency determination unit 210 checks the user's health condition from the bio signal transmitted from the mobile communication terminal 10. In general, examples of abnormal electrocardiogram include extrasystoles, atrial fibrillation, ventricular fibrillation, and paroxysmal tachycardia. As described above, various physiological phenomena can be monitored by analyzing ECG waveforms measured by the bio-signal measurement unit 110 of the mobile communication terminal 10. The emergency determination unit 210 analyzes HRV of ECG waveforms received from the mobile communication terminal 10 on time and frequency domains to monitor various bio indices and sudden cardiac death risks. In addition, the emergency determination unit 210 determines from the user's blood glucose level whether or not the user is in a shock condition.

The emergency alarm unit 220 transmits an emergency alarm signal to the mobile communication terminal 10 when it is determined to be an emergency by the emergency determination unit 210. In this case, the emergency alarm unit 220 may request a call connection from the mobile communication terminal 10.

The emergency alarm unit 220 analyzes the user's bio signal, and transmits an emergency alarm signal to another calling number according to the analysis result. When abnormal electrocardiogram is observed from the user's bio signal, the emergency alarm unit 220 transmits an emergency alarm signal to a calling number, for example, 000-1234. The mobile communication terminal 10 receives the emergency alarm signal from the calling number, and outputs a message "I am in an unconscious condition. Please help me" with a bell sound. For another example, when a shock condition is observed from the user's blood glucose level, the emergency alarm unit 220 transmits an emergency alarm signal to a calling number, for example, 000-1233. The mobile communication terminal 10 receives the emergency alarm signal from the calling number, and outputs a message "I am in hypoglycemia shock. Please give me candy or sugar" with a bell sound. As a result, it is possible to give immediate medical treatment to the user even though the user am in an unconscious condition.

The emergency alarm system further includes a short message service (SMS) server 240. The emergency alarm unit 220 transmits an emergency alarm signal with an SMS message.

The SMS server 240 is connected to a mobile switching center (MSC) to transmit an SMS message to the mobile communication terminal 10. The SMS server 240 transmits texts between text transfer systems and subscribers through a mobile communication network. The SMS server 240 generates a message based on the user's health condition transmitted from the emergency alarm unit 220, and transmits the message to the mobile communication terminal 10.

The mobile communication terminal 10 further includes a message parsing unit 180 which parses an SMS message. The control unit 120 outputs sound data corresponding to a parsed SMS message with a bell sound.

In this case, when receiving an SMS message from a phone number, the mobile communication terminal determines that the message is an emergency alarm signal, and the message parsing unit 180 parses the SMS message. When word "heart" or "blood glucose" is detected, its corresponding bell sound is output. For example, when word "heart" is detected from the SMS message, the message "I am in an unconscious condition. Please help me" is output with a bell sound. For another example, when word "blood glucose" is detected, the message "I am in hypoglycemia shock. Please give me candy or sugar" with a bell sound.

The health care server 20 further includes a subscriber data storage unit 250 which stores guardians' mobile communication terminal numbers corresponding to numbers of the mobile communication terminals 10. The emergency alarm unit 220 transmits subscriber data and an emergency alarm signal to a guardian's mobile communication terminal according to data stored in the subscriber data storage unit 250.

The subscriber data storage unit 250 may be a memory storing subscriber data and guardians' mobile communication terminal numbers. In the present embodiment, the subscriber data are stored in database.

Figure 2:
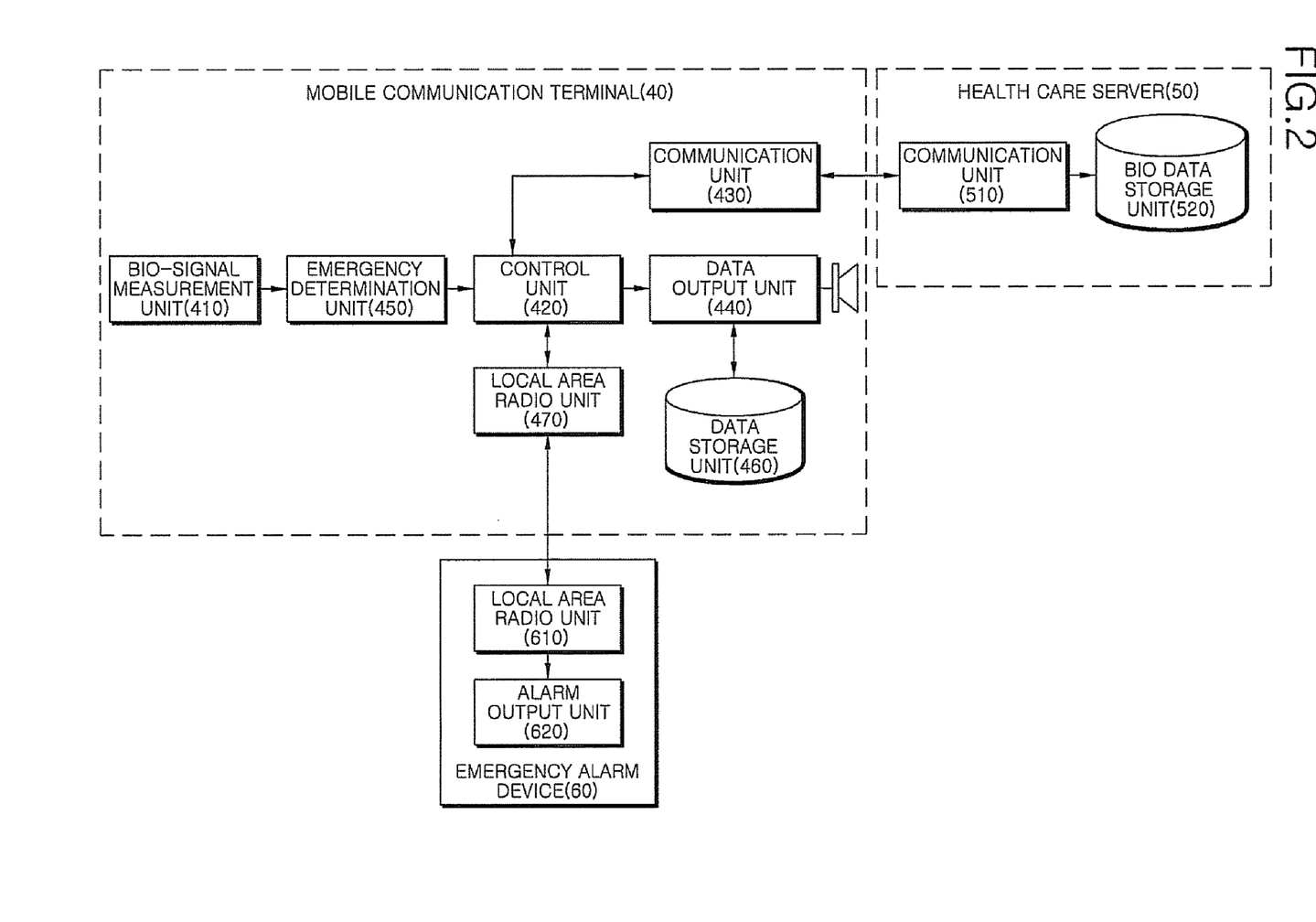
FIG. 2 is a block diagram of an emergency alarm system according to another exemplary embodiment of the present invention.

FIG. 2 is a block diagram of an emergency alarm system according to another exemplary embodiment of the present invention.

The emergency alarm system includes a bio-signal measurement unit 410, a data storage unit 460, an emergency determination unit 450, a control unit 420, and a data output unit 440. The bio-signal measurement unit 410 measures a user's bio signal. The data storage unit 460 stores sound data notifying of an emergency. The emergency determination unit 450 determines based on the bio signal measured by the bio-signal measurement unit 410 whether or not a user is in an emergency. The control unit 420 outputs one of the sound data with bell sound when it is determined to be an emergency by the emergency determination unit 450. The data output unit 440 regenerates the sound data outputted from the control unit 420 into an audible sound and outputs the audible sound through a speaker.

The bio-signal measurement unit 410 may include an ECG system. The ECG system may include an electrode unit, which includes a plurality of electrodes attached to a patient's body to detect an electric signal, an analog signal processor, which detects a bio potential from the electric signal, and a digital signal processor, which converts analog data from the analog signal processor into digital data. The bio-signal measurement unit 410 may further include other systems which measure bio signals to check the user's health condition, such as blood pressure level or blood glucose level.

The data storage unit 460 is a flash memory and stores sound data which is downloaded from a computer or a website. The data storage unit 460 stores at least one sound data to notify of the user's emergency. For example, the sound data may have voice data, such as "I am in an unconscious condition. Please help me" or "I am in hypoglycemia shock. Please give me candy or sugar".

The data storage unit 460 checks the user's health condition from the bio signal measured from the bio-signal measurement unit 410. In general, examples of abnormal electrocardiogram include extrasystoles, atrial fibrillation, ventricular fibrillation, and paroxysmal tachycardia. As described above, various physiological phenomena can be monitored by analyzing ECG waveforms measured by the bio-signal measurement unit 410. The emergency determination unit 450 analyzes HRV of ECG waveforms received from the bio-signal measurement unit 410 on time and frequency domains to monitor various bio indices and sudden cardiac death risks. In addition, the emergency determination unit 450 determines from the user's blood glucose level whether or not the user is in a shock condition.

The control unit 420 includes a digital signal processor (DSP), a microprocessor and other circuits, and generally controls the mobile communication terminal. Baseband circuits of the communication unit 430 and most circuits of the control unit 420 are provided as integrated circuits and are commercially available. The integrated circuits typically named as MSM chips include hardware dedicated for communications, digital signal processor, and common microprocessor. Components constituting the control unit 420 may be made in the form of hardware or software, or in combination of hardware and software.

When it is determined by the emergency determination unit 450 that the user is in an emergency condition, the control unit 420 outputs one of the sound data stored in the data storage unit 460 with a bell sound.

The data output unit 440 regenerates one of the sound data stored in the data storage unit 460 into an audible sound. The data output unit 440 includes a decoder, which decodes the sound data outputted from the control unit 420, a D/A converter, which converts the decoded digital audio signal into an analog signal, and a speaker, which amplifies the analog signal into an audible sound and outputs the audible sound.

Accordingly, it is possible to determine the user's health condition from the user's bio signal through the mobile communication terminal, and to promptly deal with an emergency by outputting sound data with a bell sound.

The mobile communication terminal 40 further includes a communication unit 430 which transmits a bio signal measured by the bio-signal measurement unit 410 to a health care server 50. The emergency alarm system further includes a health care server 50 which stores bio-signal data transmitted from the mobile communication terminal 40 and manages user's health conditions.

The communication unit 430 includes an antenna and an RF circuit to communicate with a base transceiver station (BTS). When a signal is received over the antenna, the communication unit 430 downconverts the signal and outputs the downconverted signal to the control unit 420. The communication unit 430 upconverts data from the control unit 420 and transmits a radio signal to the BTS over the antenna. The communication unit 430 transmits bio-signal data measured by the bio-signal measurement unit 410, or health condition data determined by the emergency determination unit 450 to the health care server 50 under the control of the control unit 420. The control unit 420 may transmit the bio-signal data measured by the bio-signal measurement unit 410 to the health care server 50 at regular intervals.

The health care server 50 is a medical center computer to monitor user's bio index. The user can check his or her bio-index graph through a website. An attending doctor can check his or her patient's bio-index graph and make a diagnosis at a remote place.

As shown in FIG. 2, the health care server 50 includes a communication unit 510 and a bio-data storage unit 520. The communication unit 510 includes an antenna and an RF circuit to communicate with a base transceiver station. The communication unit 510 receives user's bio-signal data from the mobile communication terminal 40. The bio-data storage unit 520 may be a typical memory. The bio-data storage unit 520 stores user's bio-signal data from the communication unit 510.

Accordingly, by accumulating user's bio-signal data at regular intervals, it is possible to make a more accurate diagnosis of the user based on the data.

The mobile communication terminal 40 further includes a local area radio unit 470, in which when the control unit 420 outputs sound data with bell sound and no signal is input for a predetermined time, the mobile communication terminal 40 transmits an emergency alarm output signal through the local area radio unit 470. In this case, the emergency alarm system further includes an emergency alarm device 60 including a local area radio unit 610, which receives the emergency alarm output signal from the mobile communication terminal 40, and an alarm output unit 620, which receives the emergency alarm output signal through the local area radio unit 610 and outputs an emergency alarm.

The local area radio unit 470 may be a Bluetooth module. The Bluetooth module is one which enables communication with a Bluetooth device. The local area radio unit 470 transmits an emergency alarm signal with 2.4 GHz Industrial Scientific Medical (ISM) bandwidth according to Bluetooth protocol over an antenna. The local area radio unit 470 may use IrDA or ZigBee.

The emergency alarm device 60 includes a local area radio unit 610, which receives an emergency alarm signal from the mobile communication terminal 40, and an alarm output unit 620, which outputs an emergency alarm when receiving the emergency alarm signal from the local area radio unit 610.

The local area radio unit 610 makes data communication with the local area radio unit 470 of the mobile communication terminal 40.

The alarm output unit 620 is driven with battery power of the emergency alarm device 60, and produces a sound of about 140 dB. The alarm output unit 620 preferably produces a sound larger than the mobile communication terminal 40. The emergency alarm device 60 is made in form of a wrist watch, a necklace, or an accessory of the mobile communication terminal 10 so that it is convenient for the user to carry.

Accordingly, even though it is hard to make an emergency known through the mobile communication terminal due to noise, it is possible to notify of the emergency through the emergency alarm device 60.

Figure 3:
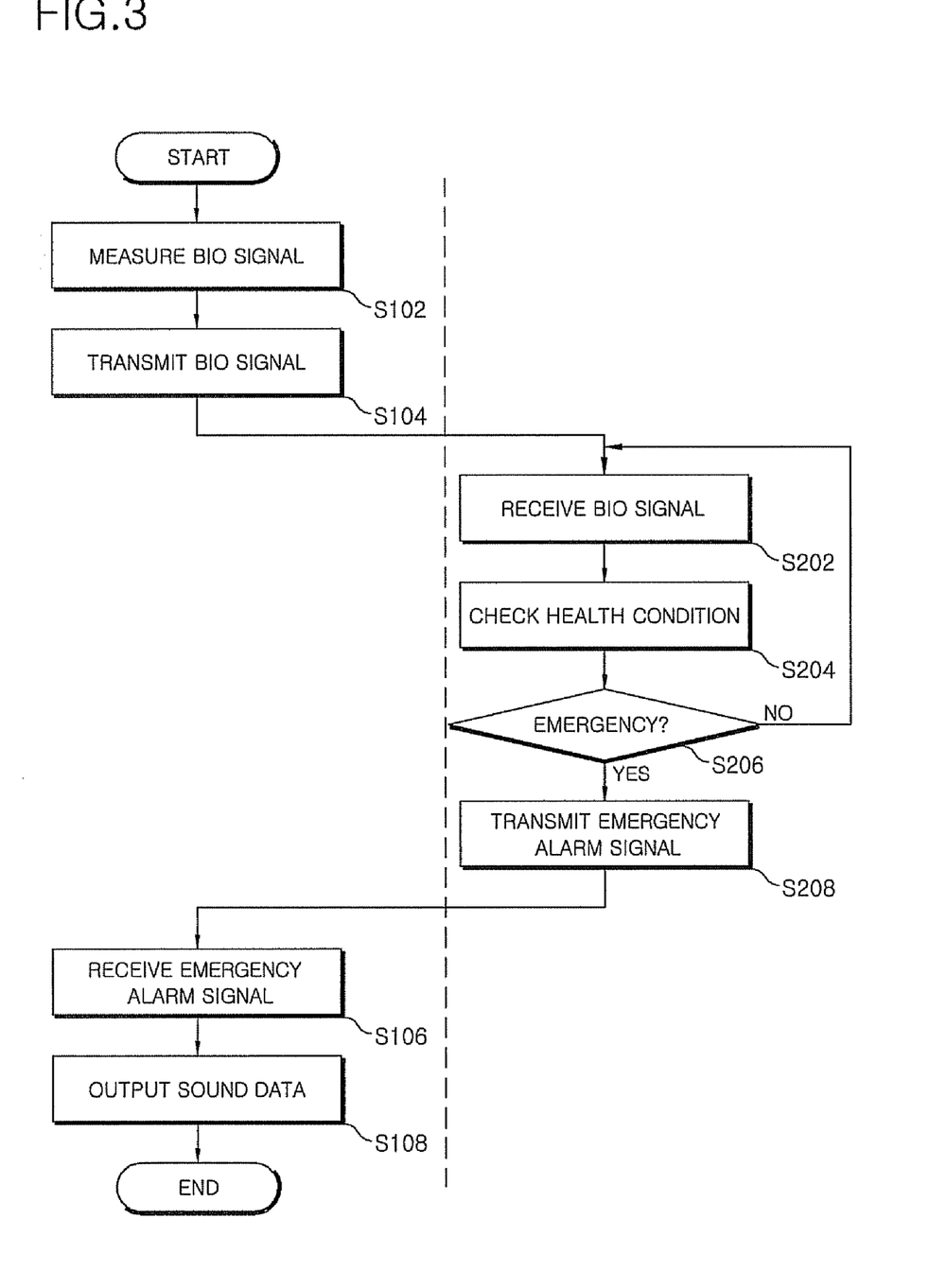
FIG. 3 is a flow chart of an emergency alarm method according to an exemplary embodiment of the present invention.

FIG. 3 is a flow chart of an emergency alarm method according to an exemplary embodiment of the present invention. The emergency is informed by a program or more which are executed on the control unit of the mobile communication terminal.

The emergency alarm method in the mobile communication terminal includes measuring a user's bio signal (step S102), transmitting the bio signal outside (S104), receiving an emergency alarm signal from the health care server (S106), and outputting sound data with a bell sound stored in the data storage unit when the emergency alarm signal is received (S108).

As described above, the bio-signal measurement unit 110 of the mobile communication terminal 10 measures a user's bio signal (S102). The bio-signal measurement unit 110 measures electrocardiogram (ECG), blood glucose, blood pressure, etc.

The control unit 120 of the mobile communication terminal 10 transmits the bio-signal data measured by the bio-signal measurement unit 110 to the health care server 20 through the communication unit 130 (S104). In this case, the bio-signal data may be transmitted on a regular interval basis or on a random basis.

When the mobile communication terminal receives the emergency alarm signal from the health care server 20 (S106), corresponding one of sound data stored in the data storage unit 160 is output with a bell sound (S108).

In the step S108, sound data corresponding to a calling number of the emergency alarm signal is output with a bell sound.

Accordingly, it is possible to receive immediate attention by outputting sound data with a bell sound corresponding to the emergency alarm signal.

The emergency alarm method in the health care server 20 will be described with reference to FIG. 3. The emergency is made known by a program or more which are executed on the health care server.

The emergency alarm method in the health care server includes receiving a bio signal (step S202), determining based on the bio signal whether or not a user's health condition is in an emergency (S206), and transmitting an emergency alarm signal to the mobile communication terminal when the user is determined to be in an emergency (S208).

As described above, the communication unit 230 of the health care server 20 receives a user's bio signal from the mobile communication terminal 10 (S202). The emergency determination unit 210 analyzes the bio signal received through the communication unit 230 and determines whether or not the user's health condition is in an emergency (S204). The emergency determination unit 210 analyzes the user's ECG heart rate variability (HRV) on time and frequency domains to monitor bio indices and the risk of sudden cardiac death. The emergency determination unit 210 may determine from the user's blood glucose level whether or not the user is in a shock condition.

The emergency alarm unit 220 generates and transmits an emergency alarm signal to the mobile communication terminal 10 (S208) when the user is determined to be in an emergency (S206).

In the step S208, the emergency alarm signal is an SMS message. The SMS server 240 generates an SMS message corresponding to the user's health condition transmitted from the emergency alarm unit 220, and transmits the message to the mobile communication terminal 10.

The mobile communication terminal 10 parses the SMS message and outputs a message with a bell sound to call for help.

As apparent from the above description, when the user's bio signal indicates that the user is in an emergency condition, sound data with bell sound is output to notify of the emergency. Accordingly, the user in an emergency condition at an unfrequented place can call for help and receive immediate attention.

In addition, the sound data with bell sound is output which corresponds to the calling number of the emergency alarm signal from the health care server based on the information stored in the mobile communication terminal. Accordingly, the user can promptly receive immediate attention in case of emergency.

In addition, since the emergency is not reported only to the user's mobile communication terminal but to the guardian's mobile communication terminal, the user can promptly receive immediate attention in case of emergency.

In addition, the mobile communication terminal can notify of an emergency without communicating with the external health care server by outputting the sound data with bell sound.

Furthermore, the user's bio signals received at regular intervals are accumulated and used to make a more accurate diagnosis of the user's health condition.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. An emergency alarm system comprising:
   a mobile communication terminal to measure and transmit a user's bio signal outside, and to output sound data with a bell sound corresponding to an emergency alarm signal when an emergency alarm signal is received from a health care server; and
   a health care server to determine whether or not the user is in an emergency condition based on the user's bio signal and transmit an emergency alarm signal corresponding to a type of emergency when the user is determined to be in an emergency,
   wherein the mobile communication terminal comprises:
   a bio-signal measurement unit to measure a user's bio signal;
   a data storage unit to store sound data notifying a type of emergency;

a communication unit to communicate with the health care server;

a control unit to transmit the bio signal measured by the bio-signal measurement unit through the communication unit and to output one of the sound data with bell sound corresponding to the type of emergency stored in the data storage unit when the emergency alarm signal is received from the health care server;

a data output unit to regenerate the sound data outputted from the control unit into an audible sound and output the audible sound through a speaker; and a phone-book storage unit to store calling numbers and sound data corresponding to the calling numbers, and the control unit selects and outputs sound data with a bell sound corresponding to a calling number of an emergency alarm signal based on the data stored in the phone-book storage unit.

2. The emergency alarm system of claim 1, wherein the control unit outputs the sound data with a maximum volume when the emergency alarm signal is received from the health care server.

3. The emergency alarm system of claim 2, wherein the mobile communication terminal further comprises a local area radio unit for local area communications, and when no signal is input for a predetermined time after the control unit outputs the sound data with a bell sound, the mobile communication terminal transmits an emergency-alarm output signal through the local area radio unit, and the emergency alarm system further comprises an emergency alarm device comprising: a local area radio unit to receive the emergency-alarm output signal from the mobile communication terminal; and an alarm output unit to output an emergency alarm when the emergency-alarm output signal is received through the local area radio unit.

4. The emergency alarm system of claim 1, wherein the health care server comprises:

a communication unit to receive a bio signal from the mobile communication terminal;

an emergency determination unit to determine based on the bio signal received by the communication unit whether or not the user is in an emergency condition; and an emergency alarm unit to generate and transmit an emergency alarm signal corresponding to a type of emergency to the mobile communication terminal through the communication unit when the user is determined to be in an emergency condition.

5. The emergency alarm system of claim 4, wherein the emergency alarm unit analyzes the bio signal and transmits an emergency alarm signal to another calling number based on the analysis.

6. The emergency alarm system of claim 4, further comprising a message server to generate and transmit a short message service (SMS) message, wherein the emergency alarm unit transmits an emergency alarm signal corresponding to a type of emergency in the SMS message through the message server.

7. The emergency alarm system of claim 6, wherein the mobile communication terminal further comprises a message parsing unit to parse the received SMS message, and the control unit outputs sound data with a bell sound corresponding to the parsed SMS message.

8. The emergency alarm system of claim 5, wherein the health care server further comprises a subscriber data storage unit to store a number of a guardian's mobile communication terminal corresponding to a number of the mobile communication terminal, and the emergency alarm unit further transmits information of the mobile communication terminal and the emergency alarm signal to the guardian's mobile communication terminal based on information stored in the subscriber data storage unit.

9. The emergency alarm system of claim 6, wherein the health care server further comprises a subscriber data storage unit to store a number of a guardian's mobile communication terminal corresponding to a number of the mobile communication terminal, and the emergency alarm unit further transmits information of the mobile communication terminal and the emergency alarm signal to the guardian's mobile communication terminal based on information stored in the subscriber data storage unit.

10. An emergency alarm method in a mobile communication terminal, the emergency alarm method comprising from the mobile communication terminal:

measuring a user's bio signal;

transmitting the bio signal outside and receiving an emergency alarm signal from a health care server, and outputting sound data with bell sound corresponding to a type of emergency stored in a data storage unit when the emergency alarm signal is received, wherein the outputting the sound data with the bell sound corresponding to the type of emergency comprises outputting sound data with the bell sound corresponding to a calling number of the received emergency alarm signal.

* * * * *